(12) United States Patent
Matlock

(10) Patent No.: US 9,872,973 B2
(45) Date of Patent: Jan. 23, 2018

(54) LUER MEMBERS FOR COAXIAL LUMEN CATHETER

(71) Applicant: Acclarent, Inc., Menlo Park, CA (US)

(72) Inventor: George L. Matlock, Pleasanton, CA (US)

(73) Assignee: Acclarent, Inc., Irvine, CA (US)

( * ) Notice: Subject to any disclaimer, the term of this patent is extended or adjusted under 35 U.S.C. 154(b) by 259 days.

(21) Appl. No.: 14/754,991

(22) Filed: Jun. 30, 2015

(65) Prior Publication Data
US 2017/0000992 A1    Jan. 5, 2017

(51) Int. Cl.
| | |
|---|---|
| A61M 29/00 | (2006.01) |
| A61M 29/02 | (2006.01) |
| A61M 39/10 | (2006.01) |
| A61M 25/00 | (2006.01) |

(52) U.S. Cl.
CPC ........ *A61M 29/02* (2013.01); *A61M 25/0097* (2013.01); *A61M 39/10* (2013.01)

(58) Field of Classification Search
CPC ...... A61M 29/00; A61M 29/02; A61M 25/10; A61M 25/1018; A61M 25/10184; A61M 2025/1061; A61M 39/10
See application file for complete search history.

(56) References Cited

U.S. PATENT DOCUMENTS

| | | | | |
|---|---|---|---|---|
| 4,588,402 A | * | 5/1986 | Igari | A61M 39/10 285/905 |
| 4,637,396 A | * | 1/1987 | Cook | A61M 25/10 604/103 |
| 5,114,423 A | * | 5/1992 | Kasprzyk | A61B 18/08 604/913 |
| 6,050,972 A | * | 4/2000 | Zadno-Azizi | A61M 25/0009 604/96.01 |
| 9,155,492 B2 | | 10/2015 | Jenkins et al. | |
| 2004/0181273 A1 | * | 9/2004 | Brasington | A61M 29/02 623/1.15 |
| 2008/0183128 A1 | | 7/2008 | Morriss et al. | |
| 2010/0030031 A1 | | 2/2010 | Goldfarb et al. | |
| 2011/0004057 A1 | | 1/2011 | Goldfarb et al. | |
| 2014/0074141 A1 | | 3/2014 | Johnson et al. | |

\* cited by examiner

*Primary Examiner* — Ashley Fishback
(74) *Attorney, Agent, or Firm* — Frost Brown Todd LLC

(57) ABSTRACT

A dilation catheter for dilation of an anatomical passageway includes a luer member, an elongate shaft, and an inflatable dilator. The luer member comprises at least one fluid port. The luer member is rotatably disposed about the elongate shaft such that the luer member is configured to rotate relative to the elongate shaft about the longitudinal axis of the elongate shaft. The elongate shaft comprises a first lumen. The at least one fluid port is in fluid communication with the first lumen such that fluid may be passed through the at least one fluid port into the first lumen. The inflatable dilator is positioned along a length of the elongate shaft. The inflatable dilator is in fluid communication with the first lumen such that the inflatable dilator is inflatable by fluid passed through the at least one fluid port and into the first lumen.

19 Claims, 16 Drawing Sheets

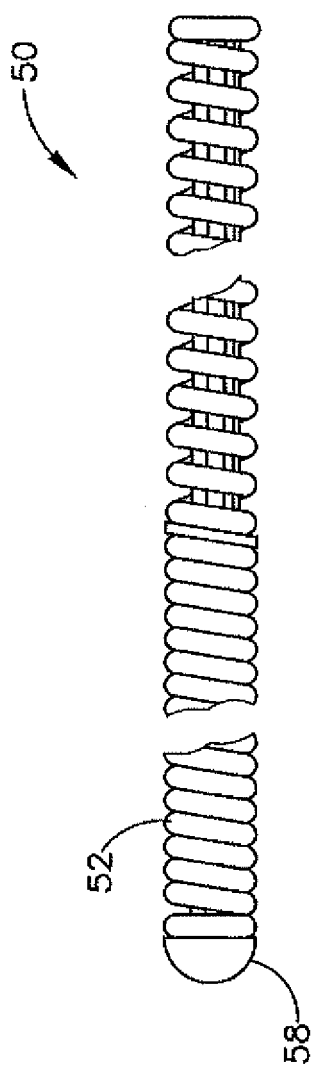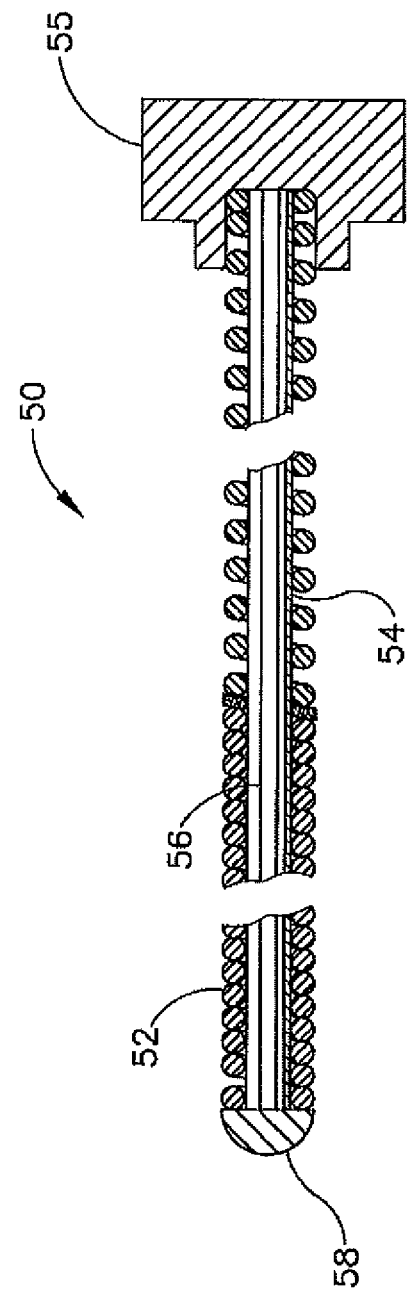

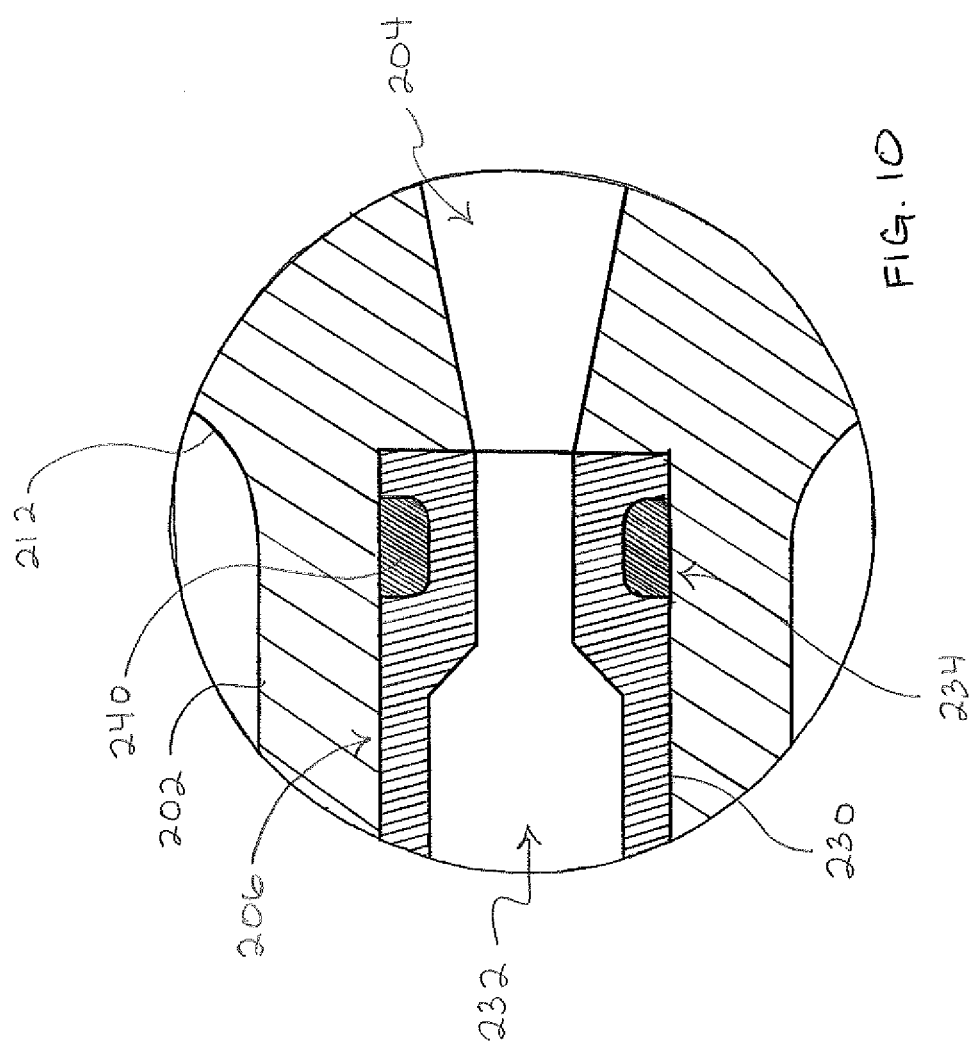

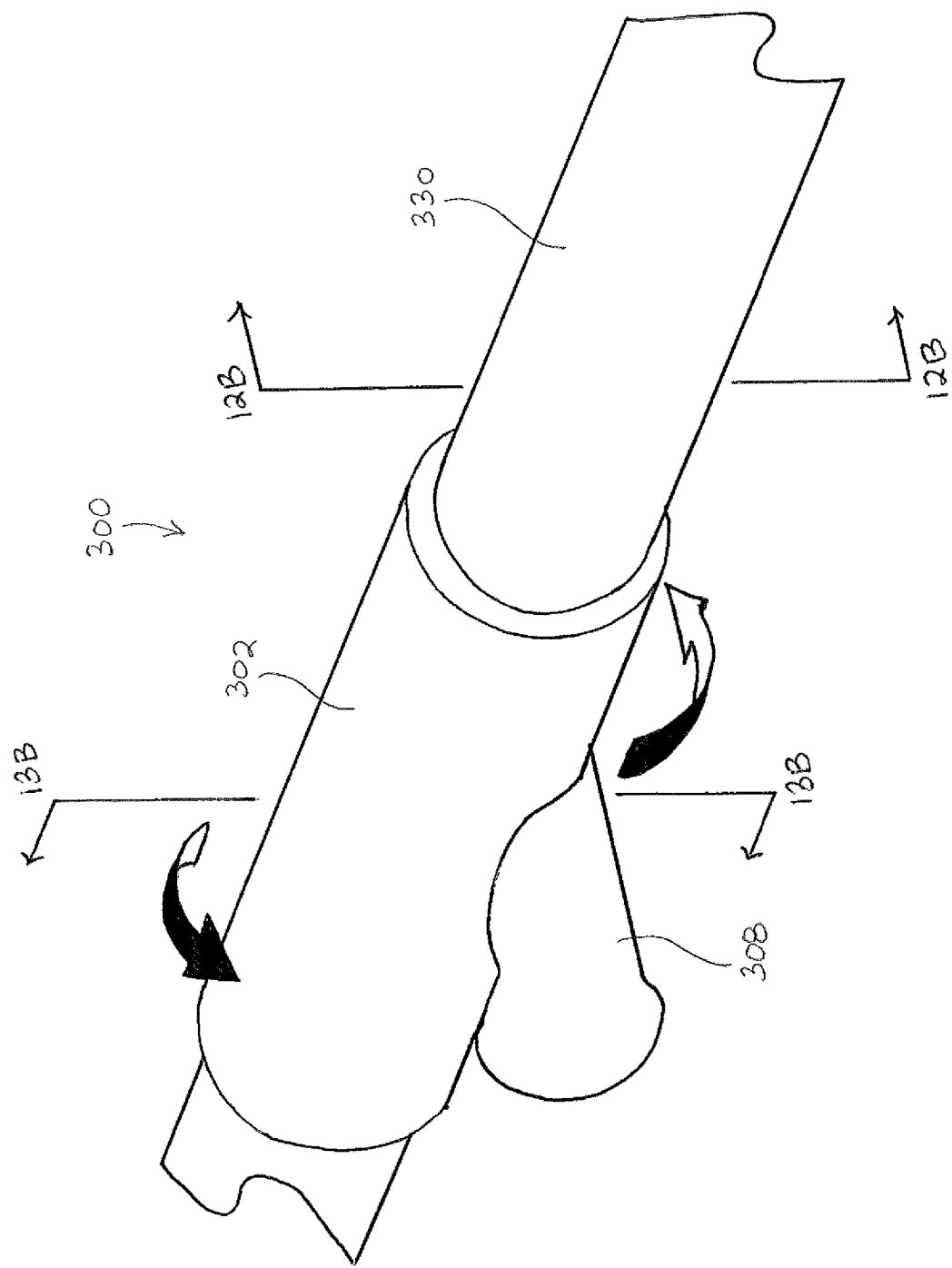

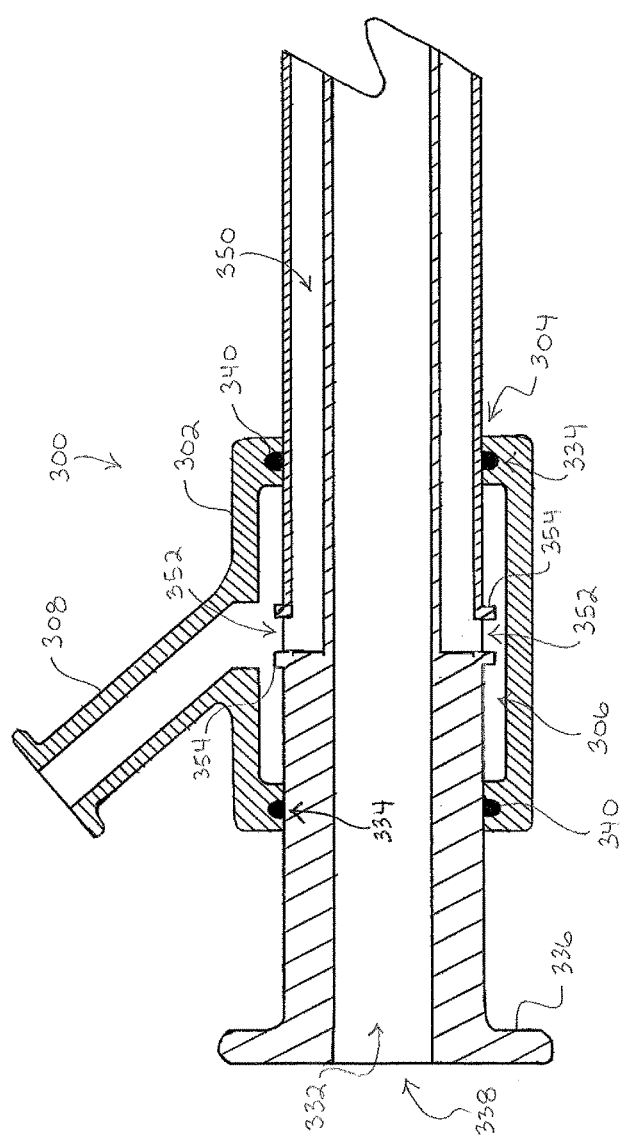

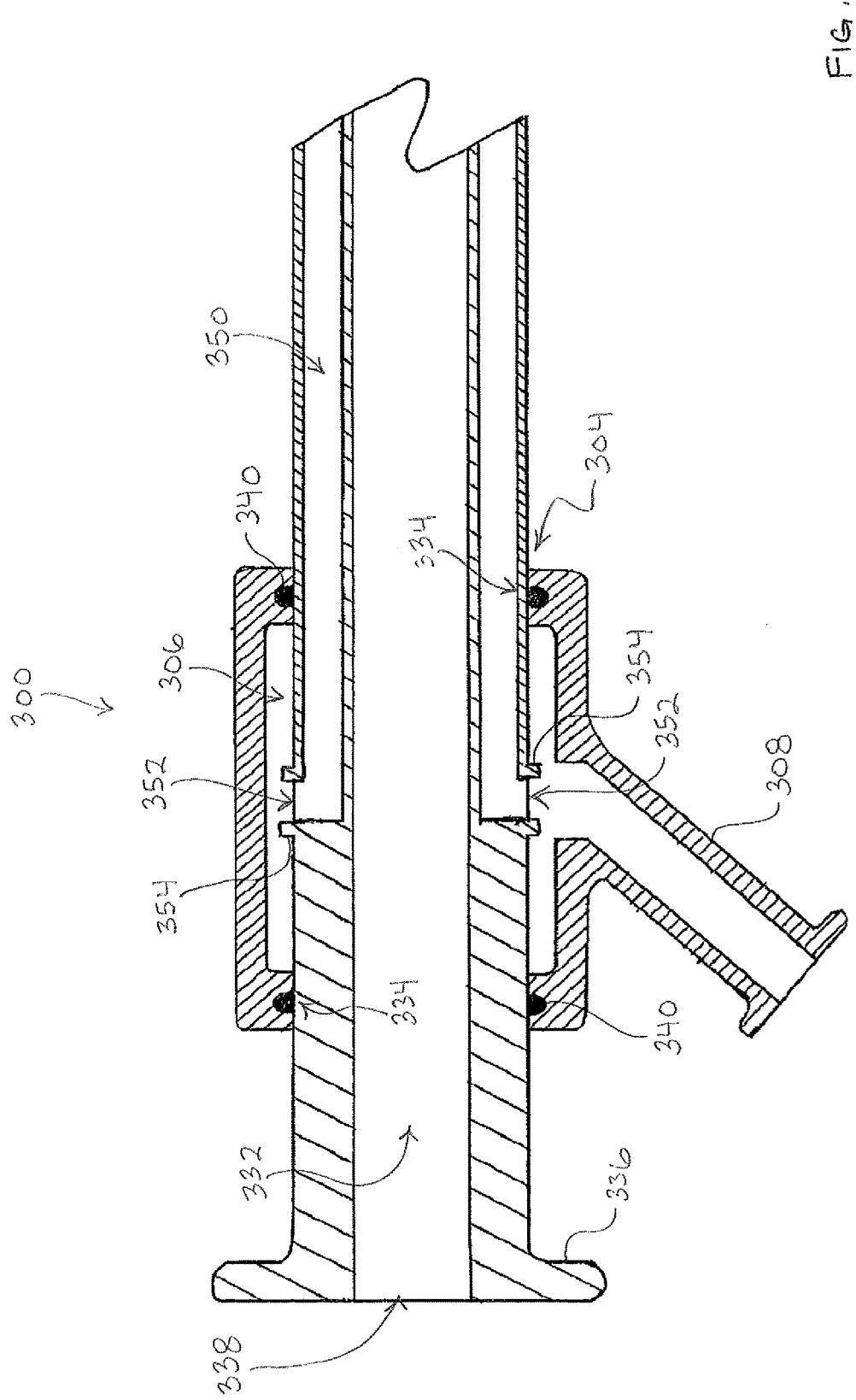

LUER MEMBERS FOR COAXIAL LUMEN CATHETER

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guide wire of FIG. 2A;

FIG. 4 depicts a detailed side cross-sectional view of the illuminating guidewire of FIG. 2A;

FIG. 10 depicts a detailed cross-sectional side view of the luer member of FIG. 8 taken along line 9-9 of FIG. 8;

FIG. 11B depicts a perspective view of the luer member of FIG. 11A, with the rotatable port of FIG. 11A rotated to a second angular position about the catheter axis;

FIG. 12A depicts a cross-sectional side view of the luer member of FIG. 11A taken along line 12A-12A of FIG. 11A, with the rotatable port of FIG. 11A in the first angular position about the catheter axis;

FIG. 12B depicts a cross-sectional side view of the luer member of FIG. 11B taken along line 12B-12B of FIG. 11B, with the rotatable port of FIG. 11A rotated to the second angular position about the catheter axis;

Figure 1:
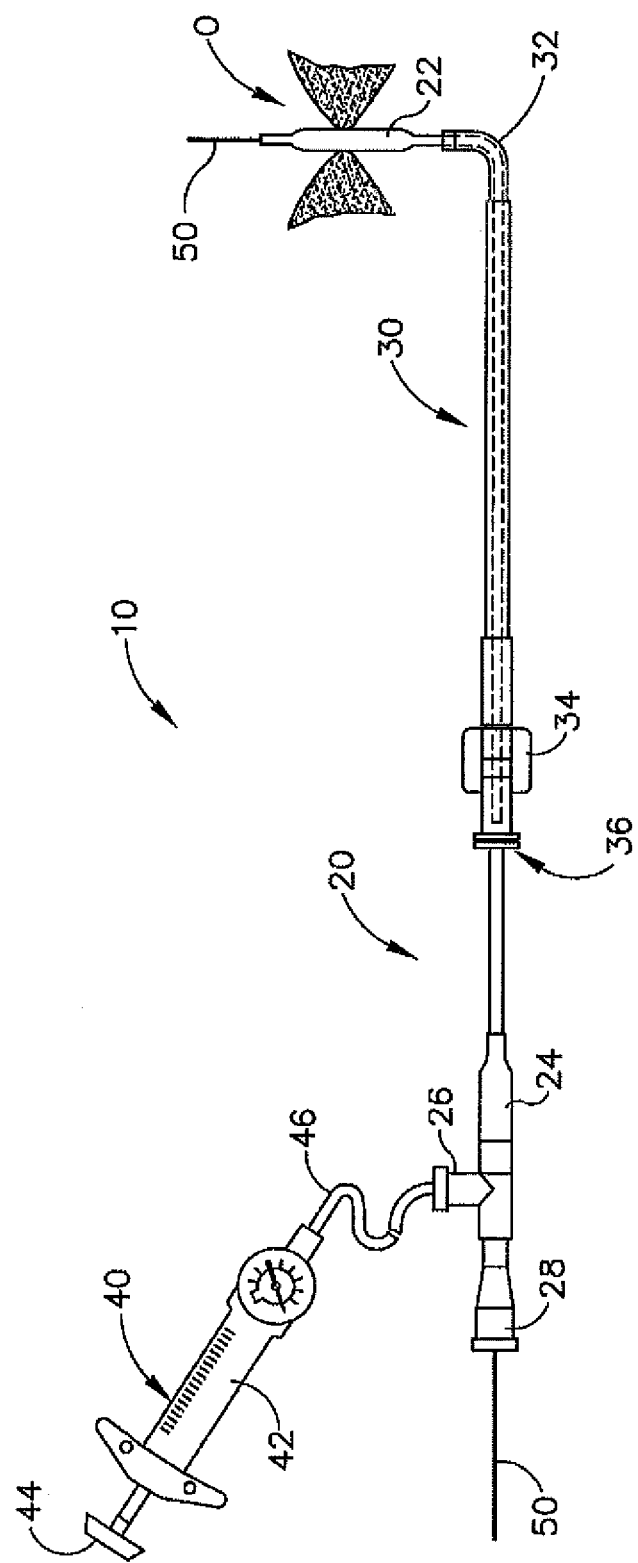
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2:
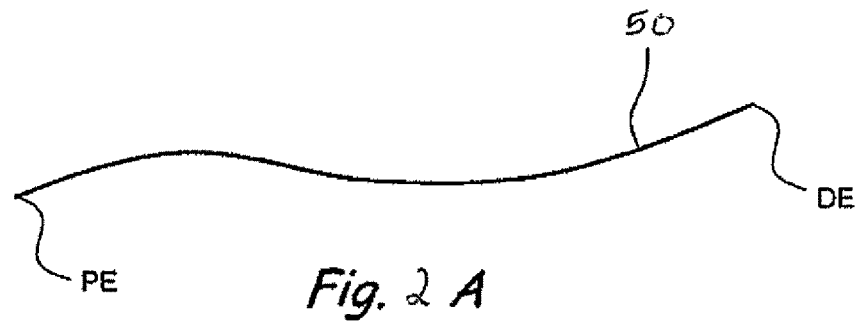
FIG. 2A depicts a side elevational view of an exemplary illuminating guidewire of the dilation catheter system of FIG. 1.
FIG. 2B depicts a side elevational view of an exemplary guide catheter of the dilation catheter system of FIG. 1.
FIG. 2C depicts a side elevational view of an exemplary dilation catheter of the dilation catheter system of FIG. 1.
Figure 2:
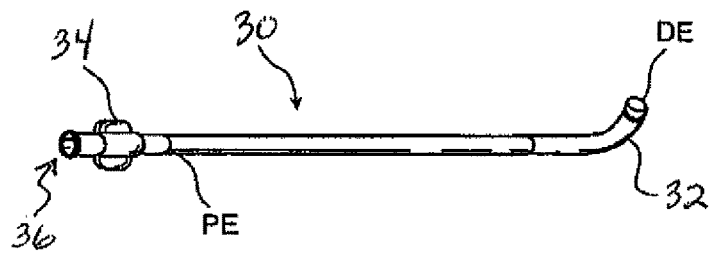
Figure 2:
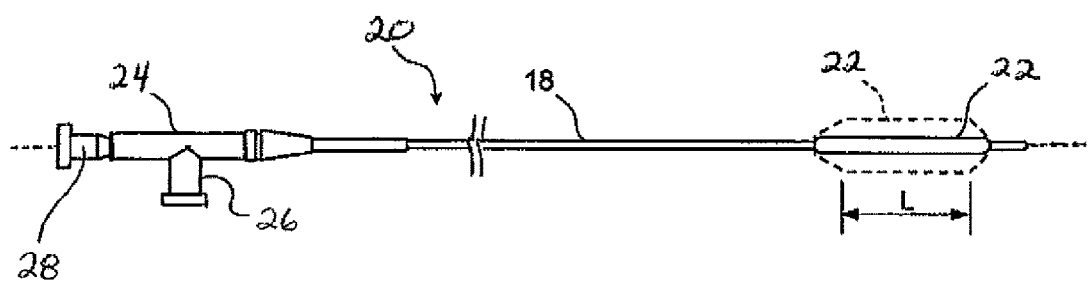

As best seen in FIG. 2C, the distal end (DE) of dilation catheter (20) includes an inflatable dilator (22). The proximal end (PE) of dilation catheter (20) includes a luer member (24), which has a lateral port (26) and an open proximal end (28). A hollow-elongate shaft (18) extends distally from luer member (24). Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to luer member (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

Figure 5:
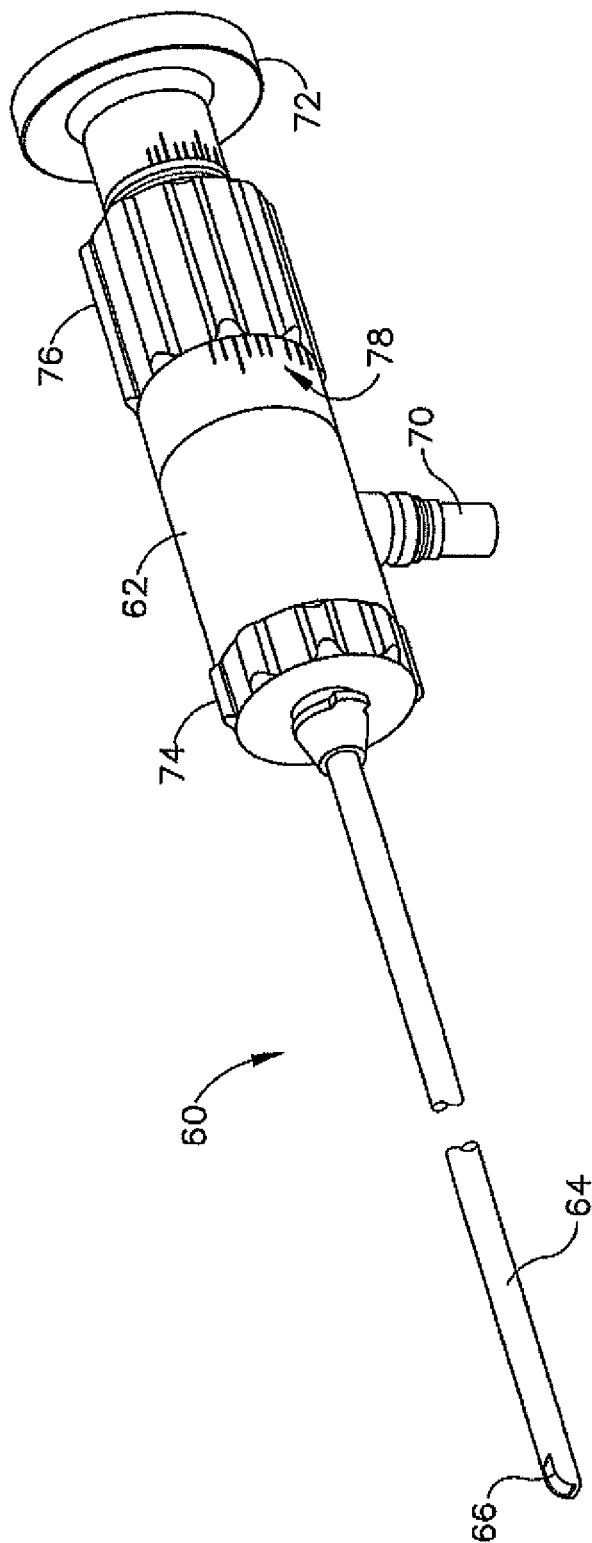
FIG. 5 depicts a perspective view of an exemplary endoscope suitable for use with the dilation catheter system of FIG. 1.
Figure 6:
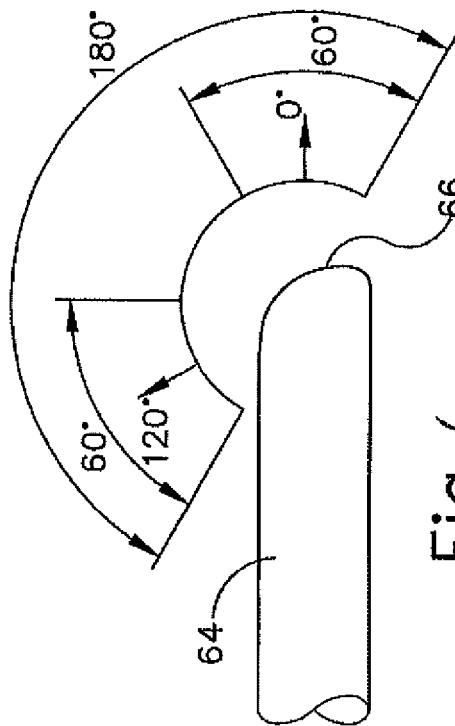
FIG. 6 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Method for Dilating the Ostium of a Maxillary Sinus FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7:
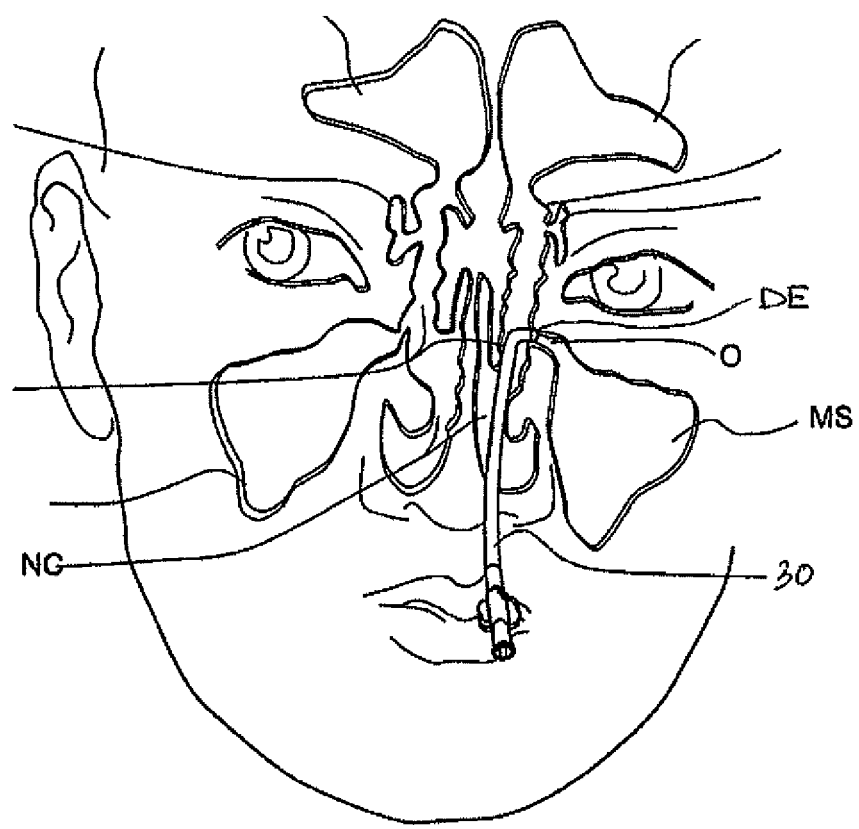
FIG. 7A depicts a front view of the guide catheter of FIG. 2B positioned adjacent an ostium of the maxillary sinus.
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.
FIG. 7E depicts a front view of an ostium of the maxillary sinus, with the ostium having been enlarged by inflation of the balloon of FIG. 7D.
Figure 7B:
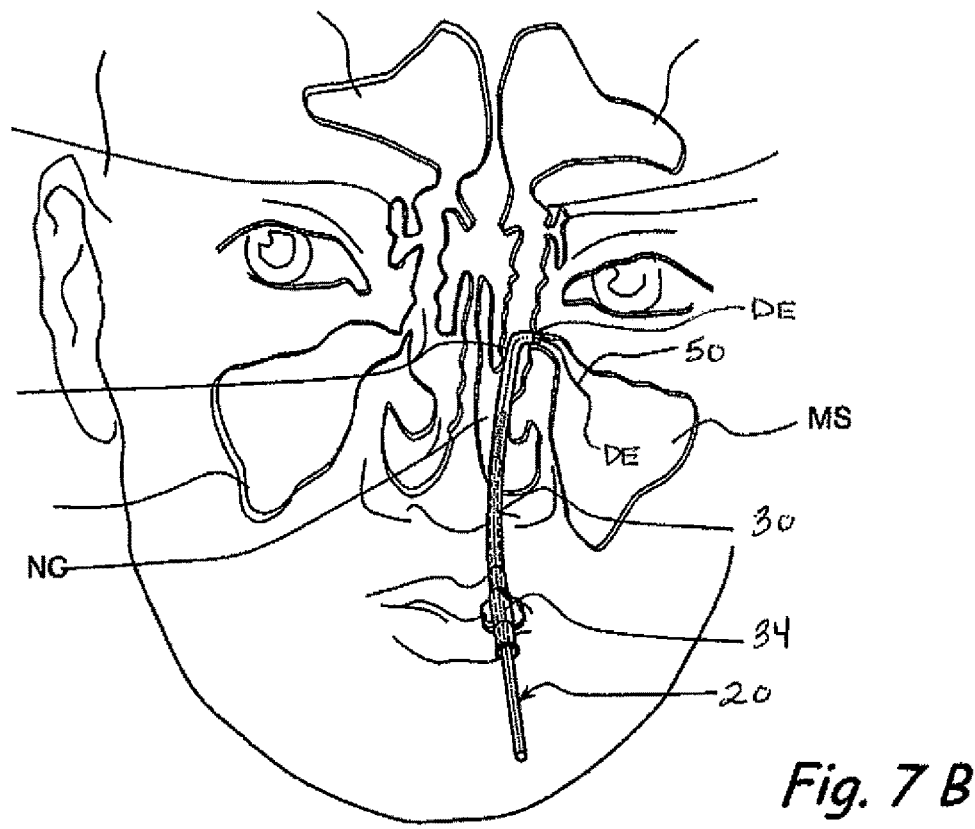
Figure 7C:
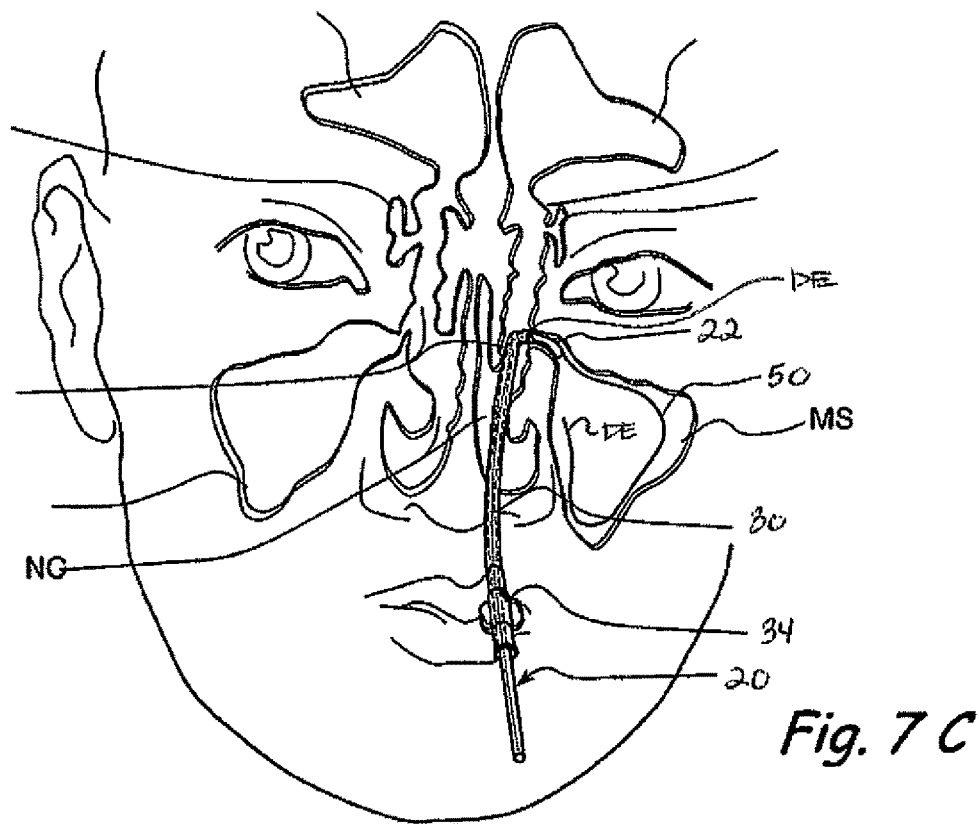

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7D:
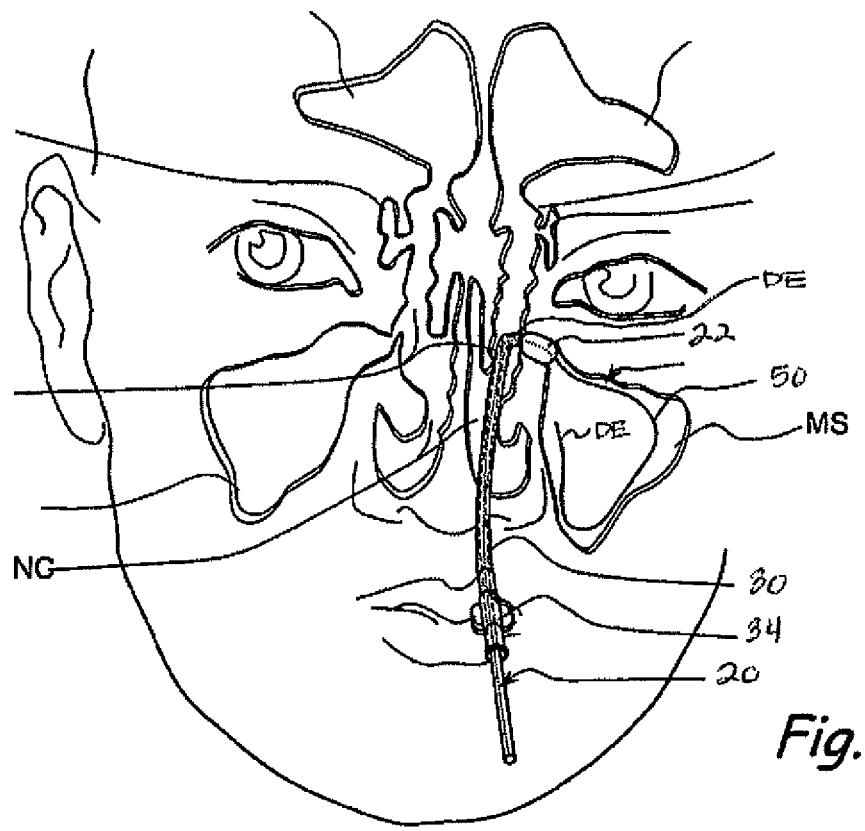
Figure 7E:
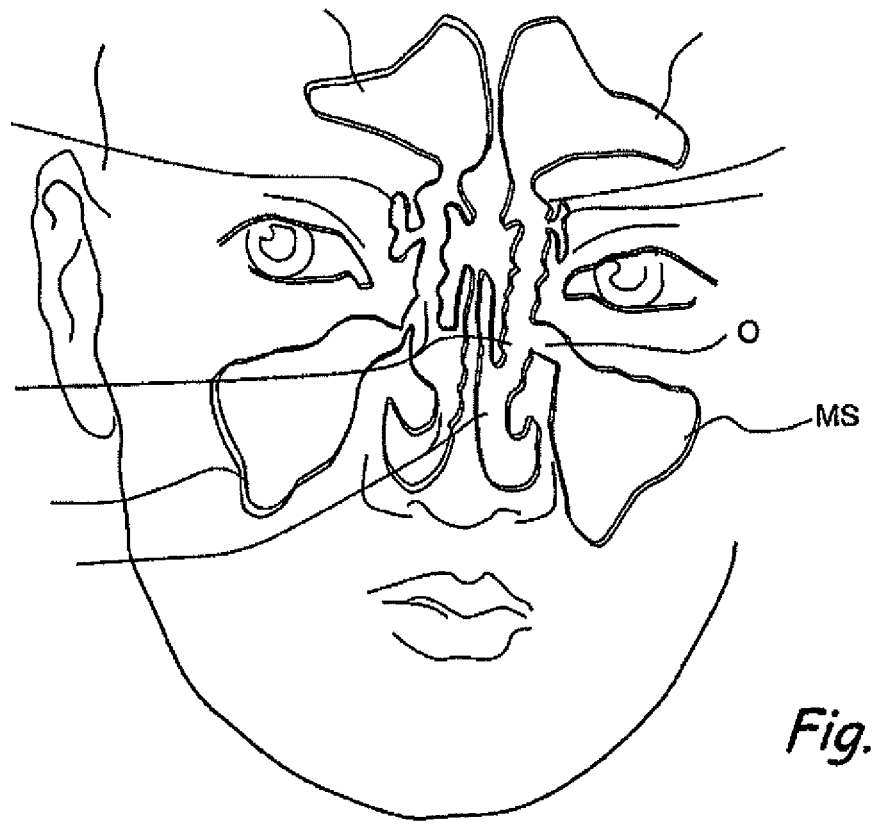

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pat. No. 7,630,676, entitled "Methods, Devices and Systems for Treatment and/or Diagnosis of Disorders of the Ear, Nose and Throat," issued Dec. 8, 2009, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

IV. Exemplary Luer Member with Durable Fluid Seal

In some versions of dilation catheter system (10) it may be desirable to provide dilation catheter (20) with features that provide for a durable and/or resilient fluid seal between luer member (24) and shaft (18). For instance, as will be described below, some versions of dilation catheter (20) may be provided with features that provide a fluid seal between luer member (24) and shaft (18) that is configured to resist dimensional fluctuations caused by thermal cycling. Various examples of such features will be described in greater detail below; while other examples will be apparent to those of ordinary skill in the art in view of the teachings herein. While the following examples are provided in the context of dilating the ostium (O) of the maxillary sinus (MS) it should be understood that the same examples may be readily applied to the context of dilating the Eustachian tube, other ostia of paranasal sinuses, the frontal recess, and/or other anatomical passageways associated with the ear, nose, and throat. Moreover, the following teachings may be applied to devices that are used in various other contexts.

Figure 8:
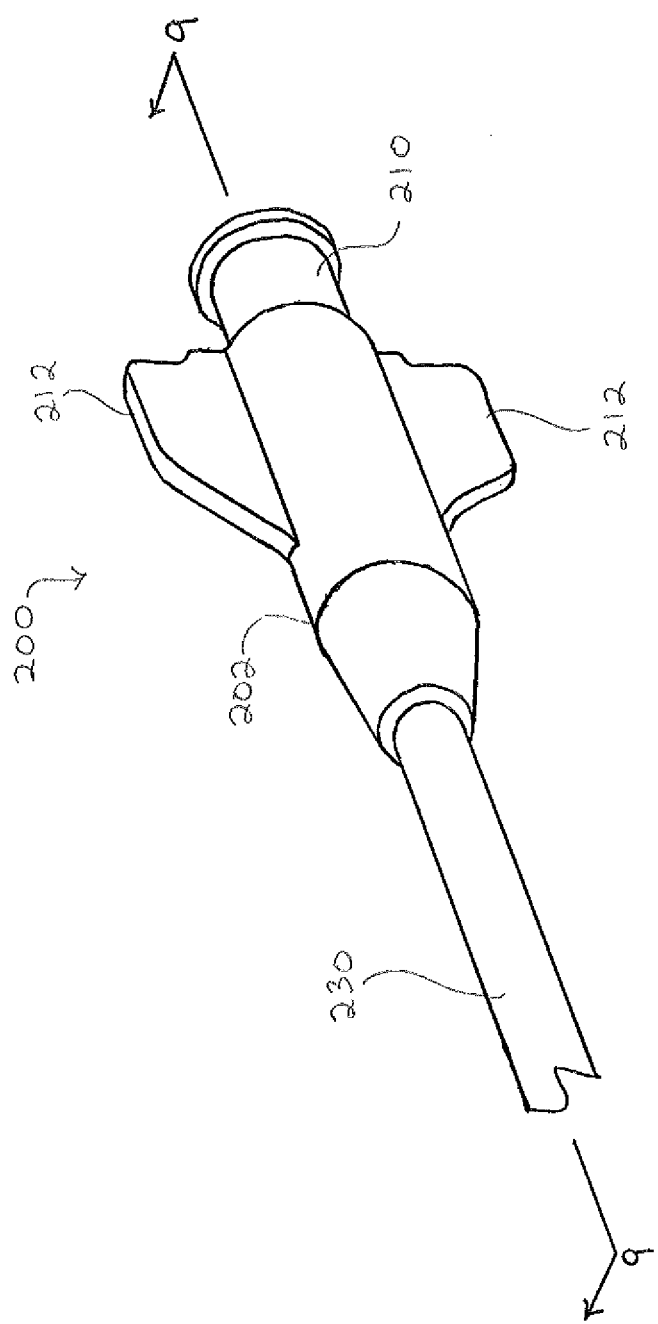
FIG. 8 depicts a perspective view of an exemplary luer member that may be incorporated into the balloon dilation catheter of FIG. 2C.
Figure 9:
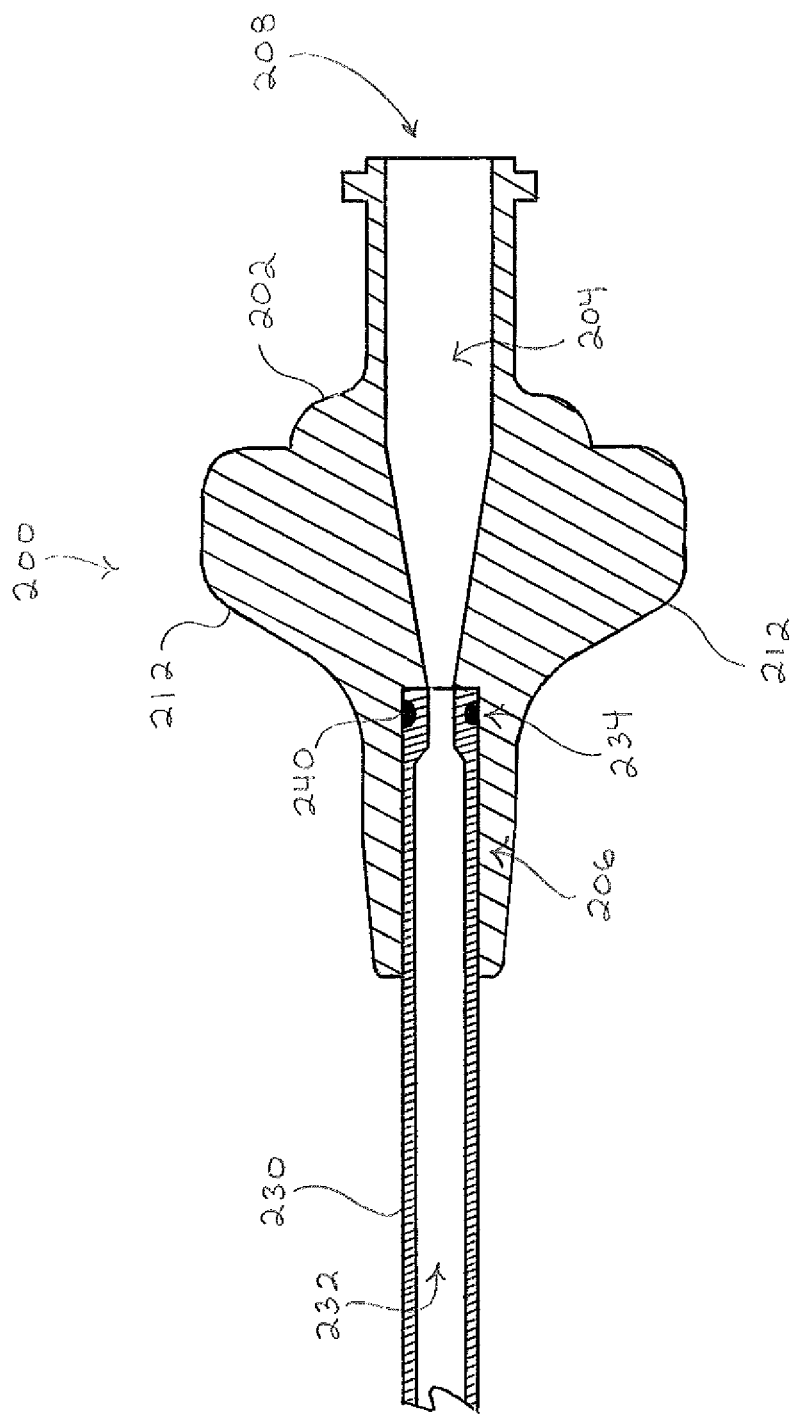
FIG. 9 depicts a cross-sectional side view of the luer member of FIG. 8 taken along line 9-9 of FIG. 8.
Figure 11A:
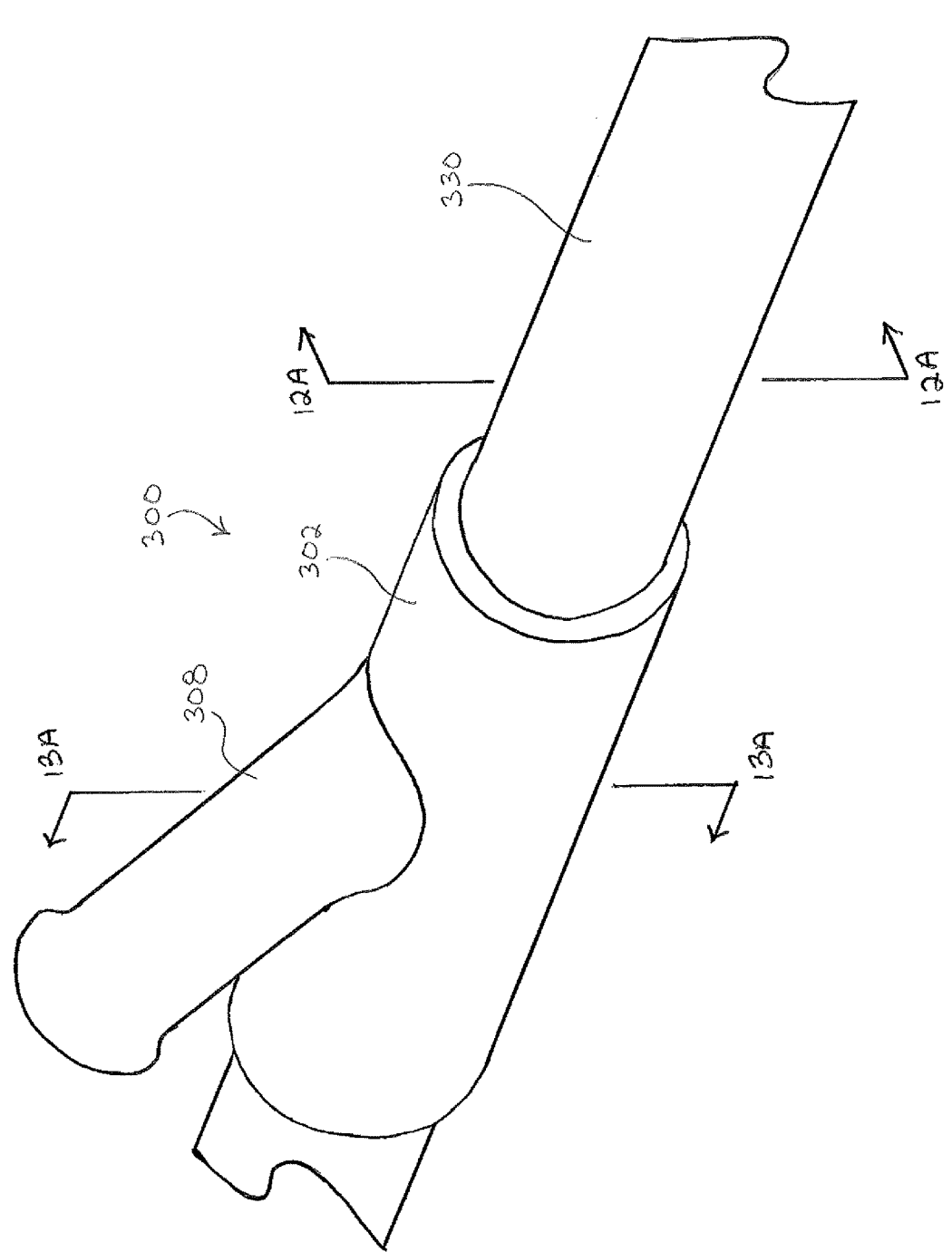
FIG. 11A depicts a perspective view of another exemplary luer member that may be incorporated into the balloon dilation catheter of FIG. 2C, with a rotatable port of the luer member in a first angular position about a catheter axis.
Figure 13A:
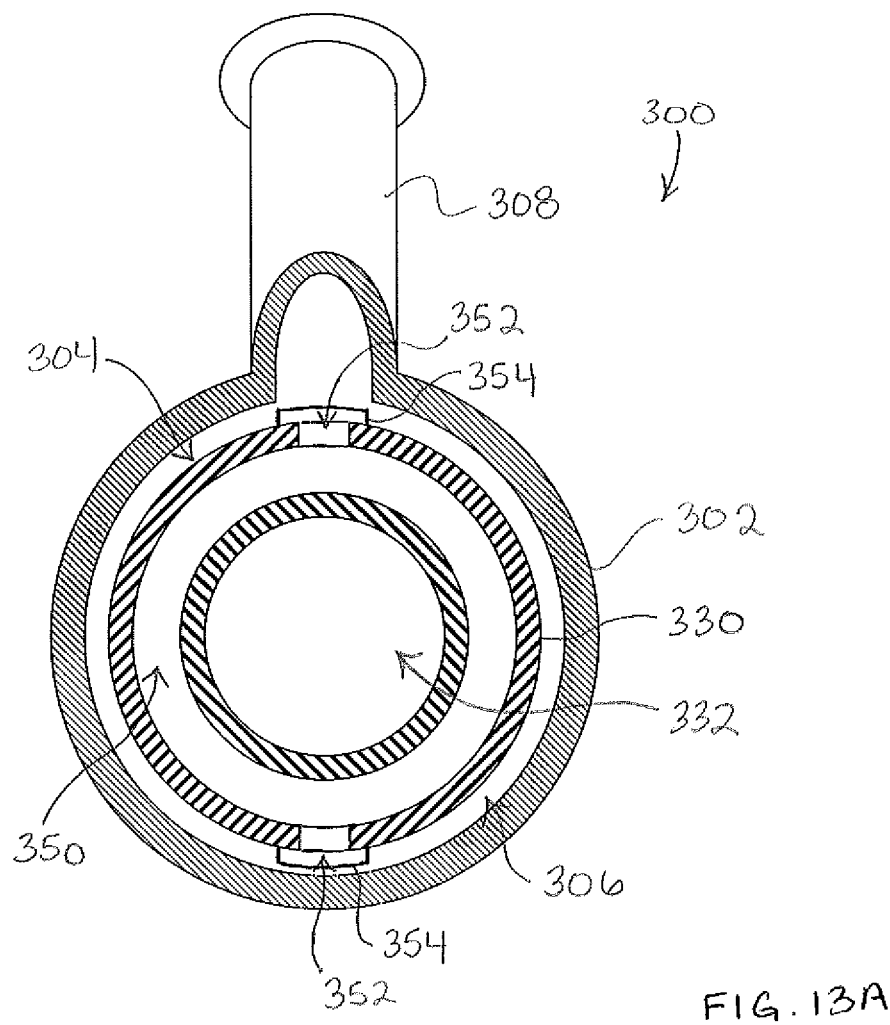
FIG. 13A depicts a cross-sectional front view of the luer member of FIG. 11A taken along line 13A-13A of FIG. 11A, with the rotatable port of FIG. 11A in the first angular position about the catheter axis.
Figure 13B:
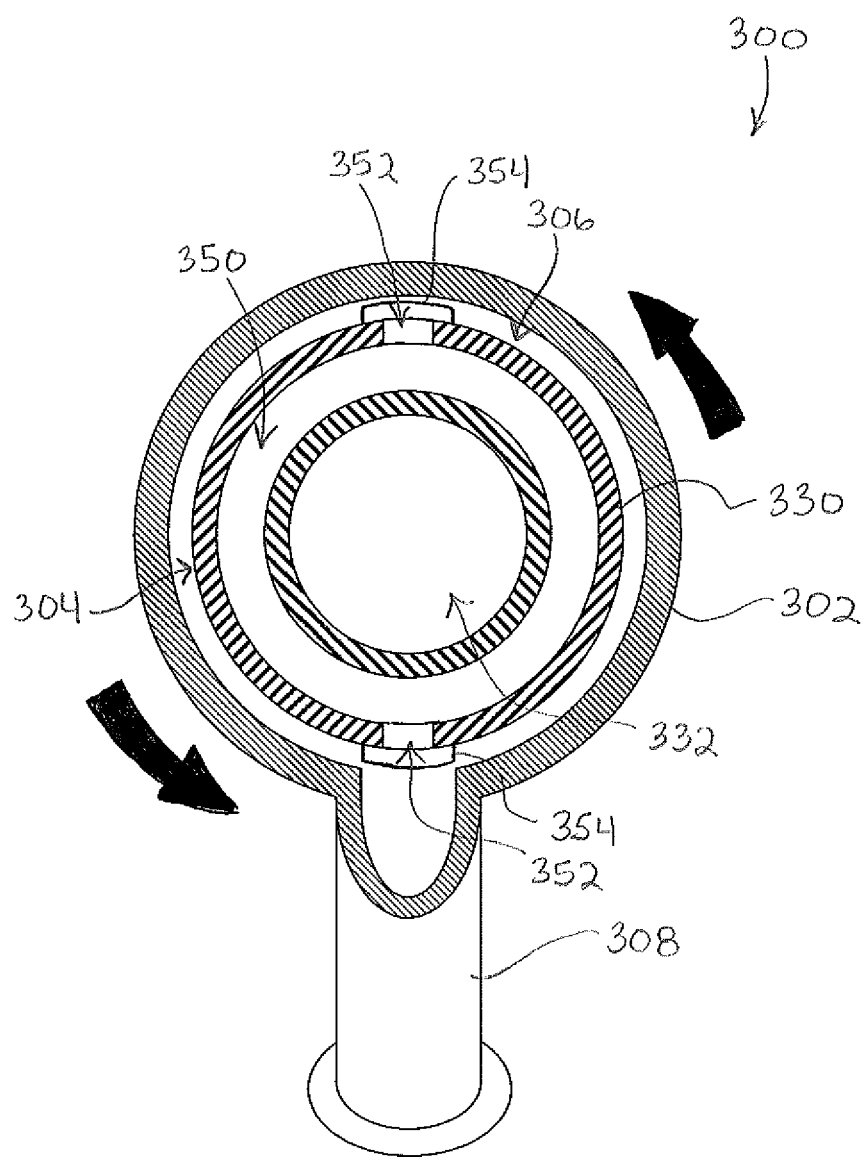
FIG. 13B depicts a cross-sectional front view of the luer member of FIG. 11B taken along line 13B-13B of FIG. 11B, with the rotatable port of FIG. 11A rotated to the second angular position about the catheter axis.

FIGS. 8-10 show an exemplary luer member (200) that may be readily incorporated into dilation catheter (20) described above, in place of luer member (24). Luer member (200) of the present example includes a body (202). Body (202) includes a pair of wings (212) extending outwardly from opposing side surfaces of body (202). Wings (212) enable an operator to better hold and maneuver luer member (200) and, as a result, dilation catheter (20). Body (202) further includes a lumen (204) extending completely therethrough and a proximal port (210), which defines an open proximal end (208) of lumen (204).

As best seen in FIG. 9, a distal portion (206) of lumen (204) is configured to receive a proximal end of a hollow elongate shaft (230), which extends distally therefrom. Shaft (230) includes a lumen (232) formed within shaft (230). Lumen (232), in conjunction with lumen (204) of body (202), provides a pathway for fluid communication between proximal port (206) and the interior of an inflatable dilator (not shown) positioned along the length of shaft (230).

As best seen in FIG. 10, a proximal portion of shaft (230) includes a annular recess (234) formed within an exterior surface of shaft (230). Annular recess (234) is formed about the entire circumference of shaft (230). Annular recess (234) is configured to receive a fluid seal (240) such as an o-ring, packing, etc. By way of further example, fluid seal (240) may comprise a molded or cast elastomeric material or lower modulus, flexible polymeric material that is a separate component inserted into the seal gland; an injection molded or cast X-ring or of a lower friction lip seal of molded or cast elastomeric material or lower modulus, flexible polymeric material that is a separate component inserted into the seal gland; an injection molded flexible sealing feature similar to a lip seal that is a molded-in feature as part of luer body (202); an o-ring of molded or cast elastomeric material or low modulus polymeric material that is insert molded onto luer body (202) in a two-step over-molded process; an o-ring of molded or cast elastomeric material or low modulus polymeric material that is formed using a dual durometer molding process; an o-ring of injection molded or cast fluoro-polymer polymeric material that is a separate component, inserted into the seal gland; or a hollow o-ring of molded or cast polymer for instances requiring a low friction sealing method, in which the hollow o-ring will inflate to create a high pressure seal as the hollow o-ring is inflated, to press against the adjacent luer body (202). Still other suitable forms that fluid seal (240) may take will be apparent to those of ordinary skill in the art in view of the teachings herein.

Fluid seal (240) is configured to provide a durable and/or resilient fluid seal between body (202) and shaft (230). It should be appreciated that, in addition to fluid seal (240), shaft (230) may include one or more secondary fluid seals positioned within the same or additional annular recesses formed within the exterior surface of shaft (230). Further, in addition to or in lieu of fluid seal (240), distal portion (206) of lumen (204) may include a primary and/or one or more secondary fluid seals positioned within one or more annular recesses formed within an interior surface of distal portion (206). Such fluid seals would be configured to provide a durable and/or resilient fluid seal between body (202) and shaft (230) in addition to or in lieu of fluid seal (240).

To secure shaft (230) within distal portion (206) of lumen (204), an adhesive may be used to create an adhesive bond between the exterior surface of shaft (230) and the interior surface of distal portion (206). In particular, adhesive may be applied to the exterior surface of shaft (230) distally of fluid seal (240) so as to create an adhesive bond between shaft (230) and distal portion (206) distally of fluid seal (240). It should be appreciated, however, that shaft (230) may be secured within distal portion (206) in any appropriate manner, not limited to the use of adhesives. For instance, shaft (230) may be secured within distal portion (206) via friction or interference fit, knurling, threading, etc. Additionally or alternatively, the proximal end of shaft (230) may be inserted into a mold for forming luer member (200) and plastic may be injected into the mold to form luer member (200) so as to attach luer member (200) to the proximal end of shaft (230). Other suitable ways in which luer member (200) may be joined with shaft (230) will be apparent to those of ordinary skill in the art in view of the teachings herein.

V. Exemplary Luer Member with Rotatable Port

In some versions of dilation catheter system (10), it may be desirable to provide dilation catheter (20) with features that facilitate repositioning of components of dilation catheter (20). For instance, as will be described below, some versions of dilation catheter (20) may be provided with features that facilitate repositioning of lateral port (26). Various examples of such features will be described in greater detail below; while other examples will be apparent to those of ordinary skill in the art in view of the teachings herein. While the following examples are provided in the context of dilating the ostium (O) of the maxillary sinus (MS) it should be understood that the same examples may be readily applied to the context of dilating the Eustachian tube, other ostia of paranasal sinuses, the frontal recess, and/or other anatomical passageways associated with the ear, nose, and throat. Moreover, the following teachings may be applied to devices that are used in various other contexts.

FIGS. 11A-13B show an exemplary luer member (300) and elongate shaft (330) that may be readily incorporated into dilation catheter (20) described above, in place of luer member (24) and shaft (18). Shaft (330) may be cast, drawn, extruded polymeric thermoset or thermos-polymer, glass, or metal tubing. Alternatively, shaft (330) may comprise any other suitable material(s) and may be formed in any other suitable fashion. Luer member (300) of the present example includes a body (302). Body (302) includes a cylindrical through bore (304). As will be described in more detail below, shaft (330) is rotatably disposed within through bore (304) of body (302) and extends distally and proximally therefrom.

As shown in FIGS. 12A and 12B, body (302) includes a pair of annular recesses (334) formed within an interior surface of through bore (304). Each circular recess (334) is configured to receive a fluid seal (340) such as an o-ring, packing, etc. By way of further example, each fluid seal (340) may comprise a molded or cast elastomeric material or lower modulus, flexible polymeric material that is a separate component inserted into the seal gland; an injection molded or cast X-ring or of a lower friction lip seal of molded or cast elastomeric material or lower modulus, flexible polymeric material that is a separate component inserted into the seal gland; an injection molded flexible sealing feature similar to a lip seal that is a molded-in feature as part of luer body (302); an o-ring of molded or cast elastomeric material or low modulus polymeric material that is insert molded onto luer body (302) in a two-step over-molded process; an o-ring of molded or cast elastomeric material or low modulus polymeric material that is formed using a dual durometer molding process; an o-ring of injection molded or cast fluoro-polymer polymeric material that is a separate component, inserted into the seal gland; or a hollow o-ring of molded or cast polymer for instances requiring a low friction sealing method, in which the hollow o-ring will inflate to create a high pressure seal as the hollow o-ring is inflated, to press against the adjacent luer body (302). Still other suitable forms that each fluid seal (340) may take will be apparent to those of ordinary skill in the art in view of the teachings herein.

Fluid seals (340) are configured to provide a fluid seal between body (302) and shaft (330). It should be appreciated that, in addition to or in lieu of fluid seals (340), shaft (330) may include one or more fluid seals positioned within one or more annular recesses formed within an exterior surface of shaft (330). Such fluid seals would be configured to provide a fluid seal between body (302) and shaft (330) in addition to or in lieu of fluid seals (340). Fluid seals (340) further permit rotation of body (302) about a longitudinal axis defined by shaft (330) such that body (302) may be selectively rotated about shaft (330). Fluid seals (340) may also permit longitudinal translation of body (302) along a length of shaft (330). In the present example, such translation of body (302) is restricted by engagement between body (302) a pair of arcuate flanges (354) extending from the exterior surface of shaft (330).

While flanges (354) are located within the interior of body (302) in the present example, in some other versions flanges (354) are positioned exterior to body (302). Flanges (354) may be molded-in features of a luer or adjacent coaxial component, or flanges (354) may be attached by adhesively attaching a flange to a molded luer component. A flange (354) may be attached using an ultrasonic, thermal, hot-air, laser or spin welding process. A flange (354) may be created using a thermal upset process, a lathe turning, a CNC machining, laser machining process A separate flange (354) may be attached using a snap, threaded or bayonet ear feature, or attached using a separate fastener using pins and holes, snap rings, or other circular metal or polymeric rings. Various other suitable ways in which flanges (354) may be formed will be apparent to those of ordinary skill in the art in view of the teachings herein.

As best seen in FIGS. 12A and 12B, through bore (304) of body (302) includes a cylindrical recess (306) formed within the interior surface of through bore (304). Cylindrical recess (306), in conjunction with fluid seals (340), defines a fluid reservoir between the exterior surface of shaft (330) and an interior surface of cylindrical recess (306). Body (302) further includes a lateral port (308) which extends obliquely from an exterior surface of body (302). In some other versions, lateral port (308) extends perpendicularly from body (302). Lateral port (308) is in fluid communication with cylindrical recess (306) such that fluid passed through lateral port (308) is communicated to cylindrical recess (306). From the description above, it should therefore be understood that lateral port (308) may be selectively rotated about the longitudinal axis of shaft (330) and/or translated along a portion of the length of shaft (330). Fluid seals (340) maintain a fluid tight interface between body (302) and shaft (330) before, during, and after any such movement of body (302) relative to shaft (330).

Shaft (330) includes a proximal port (336) which defines an open proximal end (338). Shaft (330) further includes a first lumen (332) and a second lumen (350). First lumen (332) extends from open proximal end (338) to an open distal end (not shown) that is distal to an inflatable dilator (not shown), such as dilator (22), positioned along the length of shaft (330). First lumen (332) is configured to slidably receive guidewire (50) as described above. Second lumen (350) is in fluid communication with an interior of the dilator. Second lumen (350) is further in fluid communication with cylindrical recess (306) via a pair of openings (352) that are formed in the exterior surface of shaft (330). As best seen in FIGS. 12A and 12B, translation of body (302) is limited by flanges (354) so as to maintain fluid communication between second lumen (350) and cylindrical recess (306) via openings (352). Second lumen (350) thus provides fluid communication between lateral port (308) and the interior of the dilator. Second lumen (350) coaxially positioned about first lumen (332). First and second lumens (332, 350) of shaft (330) are fluidly isolated from each other. Thus, the dilator may be selectively inflated and deflated by communicating fluid along second lumen (350) via lateral port (306) while guidewire (50) is positioned within first lumen (332).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter for dilation of an anatomical passageway, wherein the dilation catheter comprises: (a) a luer member, wherein the luer member comprises at least one fluid port; (b) an elongate shaft, wherein the elongate shaft defines a longitudinal axis, wherein the luer member is rotatably disposed about the elongate shaft such that the luer member is configured to rotate relative to the elongate shaft about the longitudinal axis of the elongate shaft, wherein the elongate shaft comprises: (i) a proximal end, (ii) a distal end, and (iii) a first lumen, wherein the at least one fluid port is in fluid communication with the first lumen such that fluid may be passed through the at least one fluid port into the first lumen; and (c) an inflatable dilator, wherein the inflatable dilator is positioned along a length of the elongate shaft, wherein the inflatable dilator is in fluid communication with the first lumen such that the inflatable dilator is inflatable by fluid passed through the at least one fluid port and into the first lumen.

Example 2

The dilation catheter of Example 1, wherein the at least one fluid port is configured to remain in fluid communication with the first lumen as the luer member rotates relative to the elongate shaft about the longitudinal axis of the elongate shaft.

Example 3

The dilation catheter of any one of Examples 1 through 2, wherein the at least one fluid port extends obliquely from an exterior surface of the luer member.

Example 4

The dilation catheter of any one of Examples 1 through 3, wherein luer member and the elongate shaft cooperate to define a fluid reservoir between an exterior surface of the elongate shaft and an interior surface of the luer member.

Example 5

The dilation catheter of Example 4, wherein the at least one fluid port and the first lumen are in fluid communication with the fluid reservoir such that fluid may be passed through the at least one fluid port into the first lumen via the fluid reservoir.

Example 6

The dilation catheter of any one of Examples 4 through 5, wherein the first lumen is in fluid communication with the fluid reservoir via at least one opening formed in an exterior surface of the elongate shaft.

Example 7

The dilation catheter of any one of Examples 1 through 6, wherein the luer member comprises at least one fluid seal configured to provide a fluid seal between the luer member and the elongate shaft.

Example 8

The dilation catheter of Example 7, wherein the at least one fluid seal comprises an o-ring.

Example 9

The dilation catheter of Example 7, wherein the at least one fluid seal comprises a pair of fluid seals.

Example 10

The dilation catheter of Example 9, wherein luer member and the elongate shaft cooperate to define a fluid reservoir between an exterior surface of the elongate shaft and an interior surface of the luer member, wherein the fluid reservoir is longitudinally positioned between the pair of fluid seals.

Example 11

The dilation catheter of any one of Examples 1 through 10, wherein the elongate shaft comprises a second lumen.

Example 12

The dilation catheter of Example 11, wherein the first lumen and the second lumen are fluidly isolated from one another.

Example 13

The dilation catheter of any one of Examples 11 through 12, wherein the second lumen extends from the proximal end of the elongate shaft to the distal end of the elongate shaft and defines an open proximal end and an open distal end.

Example 14

The dilation catheter of any one of Examples 11 through 13, wherein the second lumen is configured to slidably receive a guidewire.

Example 15

The dilation catheter of any one of Examples 1 through 14, wherein the luer member is further configured to translate relative to the elongate shaft along a length of the elongate shaft.

Example 16

The dilation catheter of Example 15, wherein the elongate shaft comprises at least one projection configured to restrict translation of the luer member along a length of the elongate shaft.

Example 17

A dilation catheter for dilation of an anatomical passageway, wherein the dilation catheter comprises: (a) a luer member, wherein the luer member comprises: (i) a proximal end, (ii) a distal end, (iii) a lumen that extends from the proximal end of the luer member to the distal end of the luer member, and (iv) at least one fluid port; (b) an elongate shaft, wherein the elongate shaft defines a longitudinal axis, wherein the elongate shaft is positioned within a distal portion of the lumen of the luer member and extends distally therefrom, wherein the elongate shaft comprises: (i) a proximal end, (ii) a distal end, (iii) a lumen formed within the elongate shaft, wherein the at least one fluid port is in fluid communication with the lumen of the elongate shaft such that fluid may be passed through the at least one fluid port into the lumen of the elongate shaft, and (iv) at least one fluid seal configured to provide a fluid seal between the luer member and the elongate shaft, wherein the elongate shaft is secured to the luer member distally of the fluid seal; and (c) an inflatable dilator, wherein the inflatable dilator is positioned along a length of the elongate shaft, wherein the inflatable dilator is in fluid communication with the lumen of the elongate shaft such that the inflatable dilator is inflatable by fluid passed through the at least one fluid port and into the lumen of the elongate shaft.

Example 18

The dilation catheter of Example 17, wherein the elongate shaft is secured to the luer member via an adhesive.

Example 19

A dilation catheter for dilation of an anatomical passageway, wherein the dilation catheter comprises: (a) a luer member, wherein the luer member comprises a fluid port; (b) an elongate shaft, wherein the elongate shaft defines a longitudinal axis, wherein the luer member is rotatably disposed about the elongate shaft such that the luer member is configured to rotate relative to the elongate shaft about the longitudinal axis of the elongate shaft, wherein the luer member and the elongate shaft cooperate to define a fluid reservoir between an exterior surface of the elongate shaft and an interior surface of the luer member, wherein the elongate shaft comprises: (i) a proximal end, (ii) a distal end, and (iii) a lumen formed within the elongate shaft, wherein the fluid port is in fluid communication with the lumen via the fluid reservoir such that fluid may be passed through the fluid port and into the lumen via the fluid reservoir; (c) a pair of fluid seals, wherein the pair of fluid seals is configured to provide a fluid seal between the luer member and the elongate shaft on opposite ends of the fluid reservoir; and (d) an inflatable dilator, wherein the inflatable dilator is positioned along a length of the elongate shaft, wherein the inflatable dilator is in fluid communication with the lumen such that the inflatable dilator is inflatable by fluid passed through the fluid port and into the lumen of the elongate shaft.

Example 20

The guidance device of Example 19, wherein the fluid seals are positioned within a pair of annular recesses formed in an interior surface of the luer member.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A dilation catheter for dilation of an anatomical passageway, wherein the dilation catheter comprises:
    (a) a luer member, wherein the luer member comprises at least one fluid port;
    (b) an elongate shaft, wherein the elongate shaft defines a longitudinal axis, wherein the luer member is rotatably disposed about the elongate shaft such that the luer member is configured to rotate relative to the elongate shaft about the longitudinal axis of the elongate shaft, wherein the elongate shaft includes a feature that is configured to restrict translation of the luer member along the length of the elongate shaft while simultaneously permitting rotation of the luer member relative to the elongate shaft, wherein the elongate shaft comprises:
        (i) a proximal end,
        (ii) a distal end, and
        (iii) a first lumen, wherein the at least one fluid port is in fluid communication with the first lumen such that fluid may be passed through the at least one fluid port into the first lumen; and
    (c) an inflatable dilator, wherein the inflatable dilator is positioned along a length of the elongate shaft, wherein the inflatable dilator is in fluid communication with the first lumen such that the inflatable dilator is inflatable by fluid passed through the at least one fluid port and into the first lumen.

2. The dilation catheter of claim 1, wherein the at least one fluid port is configured to remain in fluid communication with the first lumen as the luer member rotates relative to the elongate shaft about the longitudinal axis of the elongate shaft.

3. The dilation catheter of claim 1, wherein the at least one fluid port extends obliquely from an exterior surface of the luer member.

4. The dilation catheter of claim 1, wherein the luer member and the elongate shaft cooperate to define a fluid reservoir between an exterior surface of the elongate shaft and an interior surface of the luer member.

5. The dilation catheter of claim 4, wherein the at least one fluid port and the first lumen are in fluid communication with the fluid reservoir such that fluid may be passed through the at least one fluid port into the first lumen via the fluid reservoir.

6. The dilation catheter of claim 4, wherein the first lumen is in fluid communication with the fluid reservoir via at least one opening formed in an exterior surface of the elongate shaft.

7. The dilation catheter of claim 1, wherein the luer member comprises at least one fluid seal configured to provide a fluid seal between the luer member and the elongate shaft.

8. The dilation catheter of claim 7, wherein the at least one fluid seal comprises an o-ring.

9. The dilation catheter of claim 7, wherein the at least one fluid seal comprises a pair of fluid seals.

10. The dilation catheter of claim 9, wherein the luer member and the elongate shaft cooperate to define a fluid reservoir between an exterior surface of the elongate shaft and an interior surface of the luer member, wherein the fluid reservoir is longitudinally positioned between the pair of fluid seals.

11. The dilation catheter of claim 1, wherein the elongate shaft comprises a second lumen.

12. The dilation catheter of claim 11, wherein the first lumen and the second lumen are fluidly isolated from one another.

13. The dilation catheter of claim 11, wherein the second lumen extends from the proximal end of the elongate shaft to the distal end of the elongate shaft and defines an open proximal end and an open distal end.

14. The dilation catheter of claim 11, wherein the second lumen is configured to slidably receive a guidewire.

15. The dilation catheter of claim 1, wherein the feature comprises at least one projection.

16. A dilation catheter for dilation of an anatomical passageway, wherein the dilation catheter comprises:
(a) a luer member, wherein the luer member comprises:
   (i) a proximal end,
   (ii) a distal end,
   (iii) a lumen that extends from the proximal end of the luer member to the distal end of the luer member, and
   (iv) at least one fluid port;
(b) an elongate shaft, wherein the elongate shaft defines a longitudinal axis, wherein the elongate shaft is positioned within a distal portion of the lumen of the luer member and extends distally therefrom, wherein the elongate shaft comprises:
   (i) a proximal end,
   (ii) a distal end,
   (iii) a lumen formed within the elongate shaft, wherein the at least one fluid port is in fluid communication with the lumen of the elongate shaft through a pair of openings such that fluid may be passed through the at least one fluid port into the lumen of the elongate shaft, and
   (iv) at least one fluid seal configured to provide a fluid seal between the luer member and the elongate shaft, wherein the elongate shaft is secured to the luer member distally of the fluid seal; and
(c) an inflatable dilator, wherein the inflatable dilator is positioned along a length of the elongate shaft, wherein the inflatable dilator is in fluid communication with the lumen of the elongate shaft such that the inflatable dilator is inflatable by fluid passed through the at least one fluid port and into the lumen of the elongate shaft.

17. The dilation catheter of claim 16, wherein the elongate shaft is secured to the luer member via an adhesive.

18. A dilation catheter for dilation of an anatomical passageway, wherein the dilation catheter comprises:
(a) a luer member, wherein the luer member comprises a distal end, a proximal end, and a fluid port;
(b) an elongate shaft, wherein the elongate shaft defines a longitudinal axis, wherein the luer member is rotatably disposed about the elongate shaft such that the luer member is configured to rotate relative to the elongate shaft about the longitudinal axis of the elongate shaft, wherein the luer member and the elongate shaft cooperate to define a fluid reservoir between an exterior surface of the elongate shaft and an interior surface of the luer member, wherein the fluid reservoir terminates at the distal and proximal ends of the luer member, wherein the elongate shaft comprises:
   (i) a proximal end,
   (ii) a distal end, and
   (iii) a lumen formed within the elongate shaft, wherein the fluid port is in fluid communication with the lumen via the fluid reservoir such that fluid may be passed through the fluid port and into the lumen via the fluid reservoir;
(c) a pair of fluid seals, wherein the pair of fluid seals is configured to provide a fluid seal between the luer member and the elongate shaft on opposite ends of the fluid reservoir; and
(d) an inflatable dilator, wherein the inflatable dilator is positioned along a length of the elongate shaft, wherein the inflatable dilator is in fluid communication with the lumen such that the inflatable dilator is inflatable by fluid passed through the fluid port and into the lumen of the elongate shaft.

19. The dilation catheter of claim 18, wherein the fluid seals are positioned within a pair of annular recesses formed in an interior surface of the luer member.

* * * * *